United States Patent [19]
Lin et al.

[11] Patent Number: 5,736,331
[45] Date of Patent: Apr. 7, 1998

[54] METHOD FOR IDENTIFYING NUCLEIC ACIDS ENCODING C-FOS PROMOTER ACTIVATING PROTEINS

[75] Inventors: Stanley Li Lin, Rumson; Marnie Lynn Rothofsky, Union, both of N.J.

[73] Assignee: Schering Corporation, Kenilworth, N.J.

[21] Appl. No.: 544,900

[22] Filed: Oct. 18, 1995

Related U.S. Application Data

[63] Continuation-in-part of Ser. No. 272,412, Jul. 8, 1995, abandoned.

[51] Int. Cl.$^6$ .............................. C12Q 1/68; C12N 5/10; C07K 14/47
[52] U.S. Cl. ..................... 435/6; 435/320.1; 435/353; 435/357; 530/358
[58] Field of Search ......................... 435/240.2, 320.1, 435/6, 353, 357; 530/358

[56] References Cited

FOREIGN PATENT DOCUMENTS

WO 90/12887  11/1990  WIPO.
WO92/02639   2/1992   WIPO.

OTHER PUBLICATIONS

Asoh et al., *Proc. Batl. Acad. Sci., USA* 91:6982–6986, 1994.
Larsen et al., *Gene* 28:45–54, 1984.
LeProvost, EMBL GeneBank Accession No. X7734, 1993.
DeFeo, et al, *Proc. Natl. Acad. Sci., USA*, 78, 3328–3332 (1981).
Miller, et al, *Cell*, 36, 51–60 (1984).
Kekekar, et al, *Mol. Cell. Biol.*, 6, 7–14 (1986).
Vogt, et al, *Adv. Cancer Res.*, 55, 1–35 (1990).
Greenberg, et al, *Nature*, 311, 433–438 (1984).
Stacey, et al, *Mol. Cell. Biol.*, 7, 523–527 (1987).
O'Hara, et al, *Mol. Cell. Biol.*, 7, 2941–2946 (1987).
Fujii, et al, *Mol. Cell. Biol.*, 9, 2493–2499 (1989).
Hayes, et al, *Proc. Natl. Acad. Sci. USA*, 84, 1272–1276 (1987).
Jamal, et al, *Nature*, 344, 463–466 (1990).
Fisch, et al, *Mol. Cell Biol.*, 9, 1327–1331 (1989).
Gutman, et al, *Mol. Cell. Biol.*, 11, 5381–5387 (1991).
Vasavada, et al., *Ind. J. Biochem. Biophys.*, 25, 488–494 (1988).
Vasavada, et al., *Gene*, 55, 29–40 (1987).
Vasavada, et al., *Proc. Natl. Acad. Sci., USA*, 88, 10686–10690 (1991).
Rusconi et al., *Gene* 89, 211–221 (1990).
Cornwell, et al., *J. Biol. Chem.*, 268, 15347–15350 (1993).
Young, et al., *Biochem.*, 31, 818–824 (1992).
Riegman, et al., *Mol Endocrinol.*, 5, (No. 12) 1921–1930 (1991).
Boxer, et al., *Mol. Call. Biol.*, 9, (No. 2) 515–522 (1989).
Walsh, *Mol. Cell. Biol.*, 9, (No. 5) 2191–2201 (1989).
Barberis, et al., *Genes Dev.*, 4, 849–859 (1990).
Ohno, et al., *Proc. Natl. Acad. Sci., USA* 2945–2939 (1985).
Talmadge, et al., *Cell*, 59, 55–65 (1989).
Geller, et al., *Proc. Natl. Acad. Sci., USA*, 87, 1149 (1990.
Sambrook, et al., "Moilecular Cloning. a Laboratory Manual, 2nd ed. ", Cold Spring Harbor Press (1989).
Yanisch–Perron, et al., *Gene*, 33, 103–119 (1985).
Tooze, "DNA Tumor Viruses", 834–838 Cold Spring Harbor Press (1980).
Kirschmeier, et al. *DNA* 7, 219–225 (1988).
Sanger et al., *Proc. Natl. Acad. Sci., USA*, 74, 5463–5467 (1977).
Hirt, *J. Mol. Biol.*, 26, 365–369 (1967).
Curran, et al., *Mol. Cell. Biol.*, 3, 914–921 (1983).
Field, et al., *Mol. Cell. Biol.*, 8, 2159–2165 (1988).
Deschamps, et al., *Science*, 233, 1174–1177 (1985).
Muramatsu, et al., *Mol. Cell. Biol.*, 9, 831–836 (1989).
Housey, et al., *Cell*, 52, 343–354 (1988).
Wigler, et al., *Cell*, 11, 223–232 (1977).
Gorman, et al., *Mol. Cell. Biol.*, 2, 1044–1051 (1982).
Strickland, et al., *J. Biol. Chem.*, 266, 13364–13369 (1991).
Cooper, et al., *J. Biol. Chem.*, 259, 7835–7841 (1984).
Kuenzel, et al., *J. Biol. Chem.*, 262, 9136–9140 (1987).
Glass, et al., *J. Biol. Chem.*, 261, 2987–2993 (1986).
Kishimoto, et al., *J. Biol. Chem.*, 260, 12492–12499 (1985).
van Straaten, et al., *Proc. Natl. Acad. Sci., USA* 80, 3183–3187 (1983).
Williams, et al., *J. Biol. Chem.*, 267, (No. 13) 9035–9040 (1992).
Lacks, et al., *J. Mol. Biol.*, 114, 153–168 (1977).
Fisch, et al., *Mol. Cell. Biol.*, 7, (No. 10) 3490–3502 (1987).
Bravo, et al., *Cell*, 48, 251–260 (1987).
Perkins, et al., *Mol. Cell. Biol.*, 3, (No. 6) 1123–1132 (1983).
Lusky, et al., *Nature*, 293, 79–81 (1981).

*Primary Examiner*—James Ketter
*Attorney, Agent, or Firm*—Paul A. Thompson; Cynthia L. Foulke

[57] ABSTRACT

Materials and methods are described for identifying signal transducing molecules which activate promoters, such as the human c-fos proto-oncogene promoter, as well as antagonists of such molecules. Also described are human c-fos promoter activating proteins, and in particular novel proteins, designated CROC-1 protein and CROC-4 protein, nucleic acids encoding said proteins, and mammalian cells transfected with vectors containing such nucleic acids.

19 Claims, No Drawings

METHOD FOR IDENTIFYING NUCLEIC ACIDS ENCODING C-FOS PROMOTER ACTIVATING PROTEINS

This application is a continuation-in-part of U.S. application Ser. No. 08/272,412, filed Jul. 8, 1995, now abandoned, and also claims priority under 35 U.S.C. §119 to International Application No. PCT/US95/07874, filed Jul. 5, 1994.

The present invention relates to materials and methods for identifying signal transducing molecules which activate the human c-fos proto-oncogene promoter and antagonists of such molecules.

BACKGROUND OF THE INVENTION

Cell activation as a result of mutation or over-expression of signalling molecules, such as the proto-oncogenes Ha-ras, c-fos, c-myc, and c-jun, has been implicated in the aberrant growth of cells that forms the basis of neoplasia. See, DeFeo, et al., *Proc. Natl. Acad. Sci.*, 78, 3328–3332 (1981); Miller, et al., *Cell*, 36, 51–60 (1984); Kelekar, et al., *Mol. Cell. Biol.*, 6, 7–14 (1986); and Vogt, et al., *Adv. Cancer Res.*, 55, 1–35 (1990).

Induction of c-fos occurs in response to the activation of growth-related signalling pathways following serum stimulation of mouse 3T3 cells, or in response to overexpression of the normal and transforming versions of Ha-ras, respectively. It has also been shown that constitutive expression of c-fos occurs in certain human tumor lines. These findings suggest that the aberrant growth characteristic of the neoplastic phenotype can involve the constitutive activation of signal transduction pathways participating in c-fos proto-oncogene induction. See, Greenberg, et al., *Nature*, 311, 433–438 (1984); Stacey, et al., *Mol. Cell. Biol.*, 7, 523–527 (1987); and O'Hara, et al., *Mol. Cell. Biol.*, 7, 2941–2946 (1987).

By using c-fos promoter-driven reporter genes, specific enhancers in the c-fos proto-oncogene promoter have been identified which respond to activated signal transduction pathways. These enhancers include a tyrosine kinase responsive SCM, raf-responsive direct repeats, a protein kinase C-responsive AP-1 site, and a ras-responsive serum response element. See, Fujii, et al., *Mol. Cell. Biol.*, 9, 2493–2499 (1989); Hayes, et al., *Proc. Natl. Acad. Sci., USA*, 84, 1272–1276 (1987); Jamal, et al., *Nature*, 344, 463–466 (1990); Gutman, et al., *Mol. Cell. Biol.*, 11, 5381–5387 (1991); and Fisch, et al., *Mol. Cell. Biol.*, 9, 1327–1331 (1989).

Contingent replication systems employing transcriptional activation of the SV40 T antigen gene to identify enhancers and stably interacting transcription factors are known. See, Vasavada, et al., *Ind. J. Biochem. Biophys.*, 25, 488–494 (1988); Vasavada, et al., *Gene*, 55, 29–40 (1987); Vasavada, et al., *Proc. Natl. Acad. Sci.*, 88, 10686–10690 (1991); and Rusconi, et al., *Gene*, 89, 211–221 (1990).

Because of the importance of signalling molecules in the control of cellular proliferation, there is a need for methods to identify molecules involved in growth-related signaling systems which can in turn be used to identify biological targets for antitumor drug discovery. There is also a need for methods of identifying agents that can interfere with such growth-related signaling systems to restore normal growth when abnormal cell proliferation is occurring.

SUMMARY OF THE INVENTION

The present invention fills the foregoing needs by providing materials and methods for identifying signal transduction molecules and antagonists thereof. More specifically, this invention provides mammalian cell lines, the cells of which comprise:

(a) a recombinant vector comprising an inducible or tissue specific promoter operatively linked to a nucleic acid encoding polyomavirus large T antigen; and (b) a recombinant expression vector comprising a polyomavirus origin of replication and a nucleic acid suspected to encode an activating protein of said promoter.

Preferably the promoter is the human c-fos promoter and the activating protein is a human c-fos promoter activating protein.

The present invention further provides a method for identifying a nucleic acid encoding a promoter activating protein, comprising:

(a) culturing a mammalian cell line, the cells of which comprise:
  (i) a recombinant vector comprising an inducible or tissue specific promoter operatively linked to the coding region of the polyomavirus large T antigen gene; and
  (ii) a recombinant expression vector comprising a polyomavirus origin of replication and a nucleic acid suspected to encode an activating protein of said promoter, under conditions in which such nucleic acids are expressed; and (b) measuring the levels of replicated vectors in the cells after a period of incubation sufficient to permit vector replication;

whereby a nucleic acid encoding a human promoter activating protein is identified by measurement of increased levels of vectors in the cells.

Preferably the promoter is a human c-fos promoter and the activating protein is a human c-fos promoter activating protein.

A preferred recombinant vector comprising a human c-fos promoter for use in the present invention is the plasmid P_jLAG-8.

A preferred recombinant expression vector comprising a polyomavirus origin of replication is the plasmid Lα2.

The present invention also provides a human c-fos promoter activating proteins having the amino acid sequences defined in the Sequence Listings SEQ ID NO:1 and SEQ ID NO:3, or an antigenic fragments thereof, and nucleic acids encoding such protein or fragments.

In another embodiment, the present invention provides mammalian cell lines, the cells of which comprise:

(a) a first recombinant expression vector comprising a reporter gene operatively linked to a human c-fos promoter; and (b) a second recombinant expression vector comprising a nucleic acid encoding a human c-fos promoter activating protein.

The present invention also provides a method for identifying an antagonist of a human c-fos promoter activating protein, comprising:

(a) providing a mammalian cell line, the cells of which comprise:
  (i) a first recombinant expression vector comprising a reporter gene operatively linked to a human c-fos promoter; and
  (ii) a second recombinant expression vector comprising a nucleic acid encoding a human c-fos promoter activating protein;

(b) contacting the cell line of step (a) with a sample suspected to contain an antagonist of the human c-fos promoter activating protein; and (c) measuring the level of expression of the reporter gene; whereby an antagonist of the human c-fos promoter activating protein in the sample is identified by measurement of a reduced level of expression of the reporter gene.

Preferably the second recombinant expression vector encodes CROC-1 protein, CROC-4 protein or α2-macroglobulin receptor-associated protein.

DETAILED DESCRIPTION

All references cited herein are hereby incorporated in their entirety by reference.

The following terms are herein denoted by the indicated abbreviations: long terminal repeat (LTR); Dulbecco's modified Eagle's medium (DMEM); serum response element (SRE); chloramphenicol acetyltransferase (CAT).

All nucleic acid sequences disclosed follow the normal 5' to 3' convention, as read from left to right. Standard single-letter abbreviations are used for the nucleotide bases in the sequences (37 C.F.R. §1.822).

The term "antagonist" is defined herein as a substance that blocks or inhibits the effects of a human c-fos promoter activating protein, such as the CROC-1 protein or α2-macroglobulin receptor-associated protein.

The term "reporter gene" as used herein means either a DNA molecule isolated from genomic DNA, which may or may not contain introns, or a complementary DNA (cDNA) prepared using messenger RNA as a template. In either case, the DNA encodes an expression product that is readily measurable, e.g., by enzymatic activity, enzyme-linked immunosorbent assay (ELISA) or radioimmunoassay (RIA). Preferred reporter genes for use in the present invention include the E. coli Lac-Z gene from pCH110 (Stratagene #27-4508-01). The expression level of this gene can be measured by a sensitive fluorescent substrate assay. Also preferred is the CAT reporter gene described below, although many others well known in the art could be used instead.

The term "recombinant expression vector" means a vector prepared using recombinant techniques said vector comprising an inserted nucleic acid encoding a protein such that said vector is capable of expressing the protein upon transfection or transformation into a suitable host cell. Preferred is a vector comprising a nucleic acid encoding a promoter activating protein. Also preferred is a vector comprising a reporter gene operatively linked to a human c-fos promoter.

Cells which have been "stably transformed" have recombinant DNA incorporated into their genomic DNA. Such stably incorporated DNA is retained by the transformed cells because it is introduced into the cells with a selection marker, such as G418 resistance, which forces retention when the cells are grown in selection medium. The present invention employs transiently transfected mammalian cell lines, however stably transformed mammalian cell lines comprising a c-fos promoter-regulated large T antigen can also be used.

The inducible or tissue specific promoters of the present invention are non-housekeeping promoters, i.e., they are regulated and are not transcriptionally active under normal conditions, except to the extent that low basal levels of constitutive expression may occur.

As defined herein, "inducible promoters" are promoters the transcription activity of which is activated or enhanced in response to changes in the cellular environment that results in a cellular response, such as stress, hormonal stimulation or differentiation. Induction occurs via activation of a signalling cascade resulting in the enhanced binding and activity of transcription factors at the promoter site. Molecules involved in such induction include promoter activating proteins as described herein. Inducible promoters include the c-fos and c-myc promoters. Another inducible promoter is the multidrug resistance gene promoter described in *J. Biol. Chem.*, 268, 15347–15350 (1993).

The term "tissue specific promoter" means a promoter which is active only within a subset of cell types, such as promoters which are active only in prostate cells. See, Young, et al., *Biochem.*, 31, 818–824 (1992); and Riegman, et al., *Mol. Endocrinol.*, 5, (No. 12) 1921–1930 (1991). Other tissue specific promoters include promoters of late histone genes and promoters of muscle regulatory elements. See, *Genes Dev.*, 4, 849–859 (1990); *Mol. Cell. Biol.*, 9, 515–522 (1989); and *Mol. Cell. Biol.*, 9, 2191–2201 (1989).

Promoters that can be used in this invention include but are not limited to the promoters of the proto-oncogenes c-fos and c-myc. See, Miller, et al., supra; and Kelekar, et al., supra. Both of these promoters regulate expression in vivo of genes the overexpression of which can lead to aberrant cell growth. Most preferred is the c-fos promoter.

The term "aberrant cell growth" is herein defined as the abnormal or uncontrolled cell proliferation characteristic of neoplasms.

As used herein, the term "promoter activating protein" is defined as a protein which causes transcriptional activation of one of the above-mentioned promoters. Preferably the promoter activating protein is a human c-fos promoter activating protein. Most preferred is an activating protein having an amino acid sequence substantially identical to that of the α2-macroglobulin receptor-associated protein. Also most preferred is an activating protein having an amino acid sequence substantially identical to that of the CROC-4 protein or the CROC-1 protein, the sequences of which are defined by SEQ ID NO:3 and SEQ ID NO:1, respectively. Substantial identity of amino acid sequences means that the sequence of another c-fos promoter activating protein compared to the sequence defined by either SEQ ID NO:1 or SEQ ID NO:3 is identical or differs by one or more amino acid alterations (deletions, additions, substitutions) that do not substantially impair transcription activating activity as described herein. For example, there may be allelic or interspecies variants of the sequences defined by either SEQ ID NO:1 or SEQ ID NO:3.

Furthermore, it is well within the skill of the art, e.g., by chemical synthesis or by the use of modified polymerase chain reaction (PCR) primers or site-directed mutagenesis to modify DNA encoding a c-fos promoter activating protein having the sequence defined by either SEQ ID NO:1 or SEQ ID NO:3, to produce single or multiple base substitutions which do not substantially impair the activity of c-fos promoter activating proteins produced therefrom. Such conservatively modified variants are within the scope of this invention.

Sequence identity, is determined by optimizing residue matches, if necessary, and by introducing gaps as required. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences are typically intended to include natural allelic and interspecies variations in each respective protein sequence. Typical homologous proteins or peptides will have from 25–100% homology (if gaps can be introduced), to 50–100% homology (if conservative substitutions are included) with the amino acid sequence of the CROC-1 protein or CROC-4 protein. Homology measures will be at least about 50%, and typically at least 60% or more.

The present invention also comprises "antigenic fragments" of a human c-fos promoter activating protein. It is well known in the art that antigenic determinants (epitopes) generally contain at least about 5 amino acid residues. Ohno et al., *Proc. Natl. Acad. Sci. USA*, 82, 2945 (1985). The antigenic fragments of the invention comprise from about 5 to about 100, and preferably about 5 to about 50, amino acid residues. Whether a given polypeptide falls within the scope of this invention can readily be determined by routine experimentation using the methods described below.

Such antigenic fragments can be made by proteolysis of the whole human c-fos promoter activating protein or by chemical or recombinant DNA synthesis. The antigenic fragments can be used to elicit production of antibodies, preferably in a mammal, by standard methods. The antibodies thus produced can be used to assay for or purify the activating protein, using standard immunoassay or immunoadsorption methods.

The present invention utilizes a recombinant vector comprising the polyomavirus T antigen gene and extends the system of contingent replication to identify proteins the production of which leads to transcriptional activation of gene promoters. In contrast to the SV40 T antigen gene used by Vasavada, et al., supra, the replicating and transforming properties of the polyoma T antigen gene can be separated.

Separation of the replicating and transforming properties is accomplished by inserting a stop codon in the large T intron in a region overlapping the central coding sequences for middle T antigen. This separability of functions is important in the case of the c-fos promoter, where prevention of middle T expression eliminates the possibility of transcriptional activation of the promoter via the middle T-activated c-src- and phosphatidylinositol 3-kinase-associated signalling systems (identified in Talmage, et al., *Cell*, 59, 55–65 (1989)) due to low level, basal transcription from the promoter.

Use of the polyomavirus system enables the extension of contingent replication to several well-characterized murine systems. In contrast, the SV40 T system used by Vasavada, et al., supra, is limited primarily to simian (monkey) systems. In addition, the present system does not appear to suffer the high frequency of truncated or rearranged inserts (approximately 25 percent) previously reported for the SV40 T antigen-based system. Alteration of inserts occurs at a frequency of less than 2 percent in present system.

A preferred embodiment includes the incorporation of multiple enhancers from the promoter upstream of the polyomavirus large T antigen gene to achieve sufficient sensitivity of the promoter to permit large T induction in response to low level expression of a cDNA-encoded signalling molecule. Large T induction in turn results in plasmid replication. Co-transfection with a cDNA library as described below allows the percentage of cDNAs encoding signalling proteins to be enriched within the library population, through such large T-induced plasmid replication. The resulting enrichment permits successive screening of increasingly smaller groups of library plasmids within a cDNA library, resulting in the identification of single library plasmids encoding biologically active molecules which activate the promoter.

The self-amplification process of the present invention provides additional sensitivity towards the detection of cDNAs encoding signalling molecules. Initial plasmid replication, in response to induction, leads to enhanced expression of active signalling molecules due to greater gene copy number. This increase in signalling molecules results in greater amplification of large T antigen expression, which in turn leads to greater plasmid replication.

Preferred vectors of the present invention include novel plasmids, denoted PJAG-8 and Lα2, as described below.

The present invention further provides a method for identifying cDNAs encoding proteins which can activate a promoter, preferably a human promoter, and more preferably the human c-fos promoter. More preferred are the cDNAs, denoted CROC-1 and CROC-4, which encode c-fos promoter activating proteins. For example CROC-1 encodes a specific c-fos promoter activating protein, denoted CROC-1 protein, having the amino acid sequence shown in SEQ ID NO:1. Similarly, CROC-4 encodes a specific c-fos promoter activating protein, denoted CROC-4 protein, having the amino acid sequence shown in SEQ ID NO:3. Most preferred are the nucleotide sequences shown in SEQ ID NO:1 and SEQ ID NO:3.

The present invention also provides cDNAs encoding c-fos promoter activating proteins which are conservative mutants of the proteins encoded by CROC-1 or GROG-4. Such mutants possess the binding and c-fos promoter activating functions of the proteins encoded by CROC-1 and CROC-4, respectively.

In addition, the present invention provides compounds which are antagonists of the protein encoded by CROC-1 or CROC-4. These antagonists include proteins which are deletional, substitutional or additional mutants of the CROC-1 protein or CROC-4 protein, and which bind to, but do not activate, the human c-fos promoter.

It is recognized that, because of the degeneracy of the genetic code, there are many functionally equivalent nucleic acid sequences that can encode c-fos promoter activating proteins and c-fos promoter activating protein antagonists as defined herein. Such functionally equivalent sequences, which can readily be prepared using known methods such as chemical synthesis, PCR employing modified primers, and site-directed mutagenesis, are within the scope of this invention.

As used herein, the term "recombinant vector" includes both recombinant plasmids such as those mentioned herein and recombinant retroviral vectors, which can also be engineered as described by Geller et al., *Proc, Natl. Acad. Sci. USA*, 87, 1149 (1990).

The foregoing recombinant vectors can be used to transfect any mammalian cell capable of undergoing transfection and permitting vector replication, as herein defined. Although cells from fresh tissue explants (primary cells) could in principle be used, the use of established cell lines is preferred. Many such cell lines are available including, e.g., NIH 3T3 mouse (ATCC# CRL 1658), L-M (TK⁻) mouse (ATCC# CCL 1.3) and BALB/c 3T3 Clone A31 mouse (ATCC# CCL 163) cell lines.

The choice of a cell or cell line for use in the methods of the present invention will be dictated by the known or determinable specificities of the vectors used. For example, the murine cell lines are preferred for use with vectors comprising a recombinant vector containing the polyomavirus large T antigen gene under the control of a regulated promoter, such as the human c-fos promoter; and a mammalian recombinant expression vector comprising a polyomavirus origin of replication and a nucleic acid suspected to encode a human promoter activating protein, such as a retroviral expression vector comprising a retroviral LTR capable of expressing the nucleic acid.

Although cells for use in the present invention were transiently transfected, stably-transformed cells can also be used. Stable transformation of a mammalian cell line can be accomplished by using standard methods to co-transfect the cells with one of the above-mentioned recombinant vectors and with a second vector which confers resistance to a selection agent such as an antibiotic.

To identify nucleic acids encoding human c-fos promoter activating proteins using the methods of this invention, cells are co-transfected with a recombinant vector comprising a human c-fos promoter operatively linked to polyomavirus large T antigen gene, and a cDNA library incorporated into a mammalian recombinant expression vector comprising a polyomavirus origin of replication. The cells are then incubated under conditions in which vectors containing cDNA encoding a human c-fos promoter activating protein will stimulate increased vector replication. The cells are then harvested, the plasmids extracted and unreplicated vectors selectively digested with DpnI. Replicated plasmids are recovered by transforming competent bacteria with the DpnI digest.

Typical incubations are carried out for 2 days at 37° C. in a humidified $CO_2$ incubator, although the choice of conditions will be apparent to those skilled in the art and will depend, e.g., upon the nature of the cells, the medium used and the type of culture container. Incubation is continued for a period of time sufficient to permit development of a strong replicative response. The optimal time is determined by routine experimentation but will typically be in the range of about 24 to 72 hours.

A substantially increased level of vector replication and recovery after DpnI digestion will be detected for those vectors comprising nucleic acids encoding human c-fos promoter activating proteins as compared to background resulting from replication of vectors lacking such nucleic acids.

A substantial increase in vector replication and recovery is typically an increase of at least about 5-fold, preferably about 8-fold, and most preferably about 20-fold, above the level measured in the complete absence of a plasmid comprising a nucleic acid encoding a human c-fos promoter activating protein. The degree of increase will be primarily dependent upon the level of background replication.

Substantially the same procedures are used for identifying nucleic acids encoding other human promoter activating proteins, by utilizing vectors comprising the promoter operatively linked to a nucleic acid encoding polyomavirus large T antigen.

In screening human c-fos promoter activating protein antagonists using the methods of this invention, cells are provided which are simultaneously transfected with a first recombinant expression vector comprising a reporter gene operatively linked to a human c-fos promoter and a second vector comprising a nucleic acid encoding a human c-fos promoter activating protein. Preferred reporter genes are the fos-CAT reporter gene described below or a fos-lac Z reporter gene. The cells are planted in a culture medium appropriate to the kind of cells used.

The cells are then incubated in the absence (control) or presence of varying quantities of samples containing suspected antagonists under conditions in which the gene encoding the human c-fos promoter activating protein is expressed. Under such conditions, and in the absence of an antagonist, stimulation of the human c-fos promoter will occur, resulting in reporter gene expression. The samples can be, e.g. aqueous or water-miscible solutions in which isolated compounds have been dissolved, or individual or pooled fractions from purification steps such as chromatographic or electrophoretic fractions.

Typical incubations are carried out at about 37° C. in a humidified $CO_2$ incubator, although the choice of conditions will be apparent to those skilled in the art and will depend, e.g., upon the nature of the cells, the medium used and the type of culture container.

Incubation is continued for a period of time sufficient to permit significant reporter gene induction, at which time the level of expression of the reporter gene is measured by an appropriate assay. The optimal time for making the measurement is determined by routine experimentation but will typically be in the range of about 24 to 72 hours, preferably about 48 hours.

The highest levels of reporter gene expression will be measured in the control (antagonist free) cultures. Where a culture contains a human c-fos promoter activating protein antagonist, a reduction in the level of reporter gene expression will be measured, the degree of which will be a direct function of the quantity of antagonist added to the medium. Antagonists present in the samples added to some of the cultures will be identified by measuring a substantially decreased level of reporter gene expression, compared to the level measured in the control cultures.

A substantially decreased level of reporter gene expression is defined as a decrease of at least about 50%, and preferably at least about 70%, of the level measured in the complete absence of an antagonist of a human c-fos promoter activating protein. Of course, the degree of decrease may be influenced by the quantity of antagonist present in the sample compared to the quantity of human c-fos promoter activating protein used and the efficiency of the antagonist.

Decreased levels of reporter gene expression due to general toxicity of samples can be accounted for by transfecting a second constitutively expressed reporter gene, such as lac-Z driven by a β-actin promoter and normalizing c-fos reporter gene activity to lac-Z expression.

The following non-limiting Examples will serve to illustrate the present invention.

EXAMPLES

Materials and General Methods:

Unless otherwise specified, percentages given below for solids in solid mixtures, liquids in liquid mixtures, and solids in liquids are on a wt/wt, vol/vol and wt/vol basis, respectively. Sterile conditions are maintained during cell culture.

Standard recombinant methods were used throughout, such as those described in Sambrook, et al., "Molecular Cloning. A Laboratory Manual, 2 ed.", Cold Spring Harbor Laboratory Press (1989).

DpnI is a known restriction endonuclease isolated from *Diplococcus pneumoniae* and is commercially available from ICN Biomedicals, Sigma Chemical Company or New England BioLabs, Inc.

The restriction endonucleases AseI, BamHI, BglII, BstXI, ClaI, FspI, HincII, NarI, NotI, SacII, SalI, ScaI, XbaI and XhoI are known and are commercially available, e.g. from Sigma Chemical Company.

The restriction endonucleases BamHI, BssHII, BstXI, HincII, SalI, ScaI and XbaI are known and are commercially available, e.g. from ICN Biomedicals.

The restriction endonucleases AflIII, AseI, BamHI, BglII, BssHII, BstXI, ClaI, FspI, HincII, NaeI, NarI, NotI, SacII, SalI, ScaI, XbaI and XhoI are known and are commercially available, e.g. from New England BioLabs, Inc.

The restriction endonuclease SauI is known and is commercially available, e.g. from Boehringer Mannheim.

The enzyme mung bean nuclease is known and is commercially available from New England BioLabs, Inc. or Sigma Chemical Company.

The synthetic polylinker used in preparing the vector Lα2 was obtained from New England BioLabs, Inc. and has the sequence shown in SEQ ID NO:2. The NcoI linker d(pAGCCATGGCT) is known and is commercially available from New England Biolabs, Inc. (catalog #1150).

The vector pUC19 (ATCC 37254, GenBank Accession #: X02514) is commercially available from New England BioLabs, Inc. or ICN Biomedicals. The nucleotide sequence and restriction sites of pUC19 are described by Yanisch-Perron, et al., in Gene, 33, 103–119 (1985).

The following DNA, utilized in preparing the plasmids of the present invention, is publicly available: Polyomavirus DNA strain A2 (ATCC #45017); and human genomic c-fos (ATCC #41042). In addition, the DNA sequence of polyomavirus strain A2 is reported in DNA Tumor Viruses, ed. Tooze, J. (1980) (Cold Spring Harbor Press), pp. 834–838.

Construction of the retroviral vector pMV7 is described by Kirschmeier, et al., DNA, 7, 219–225 (1988), starting from plasmids pPyori and pMV (ATCC#37190). The vector pMV7 is well known in the art and has been freely and widely distributed in many laboratories. In addition, retroviruses similar to pMV7 which could be used instead in this invention are readily available, such as pV-mos (ATCC# 41037).

The fos-CAT reporter gene construct described below was prepared using the commercially available pCAT-basic vector (Promega catalog #E1041).

Mouse monoclonal antibodies directed against the hemagglutinin epitope and fluorescein-conjugated rabbit anti-mouse IgG are commercially available from Boehringer Mannheim.

For cDNA library screening a unidirectional cDNA library was made from human brain poly A RNA (Clontech, Palo Alto, Calif.) using the GIBCO (Grand Island, N.Y.) Superscript cloning kit, and inserted into the SalI/NotI sites in plasmid Lα2.

Separation and visualization of nucleic acids was carried out as described in Sambrook, et al., supra, by electrophoresis on agarose gels and visualization with ethidium bromide. All nucleotide sequencing was performed using the dideoxy-mediated chain termination method described in Sanger, et al., Proc. Natl. Acad. Sci. USA, 74, 5463–5467 (1977). To obtain the sequences of CROC-1 and CROC-4, DNA sequencing was performed on both strands.

Co-transfection of cells with $P_fLAG$ and Lα2 containing a cDNA encoding a biologically active signalling molecule causes activation of the c-fos promoter, resulting in the production of large T antigen. The production of large T antigen stimulates intercellular replication of plasmids containing the polyomavirus origin of replication. Plasmids are recovered from the transfected cell cultures by "Hirt extraction" using the methods described in Hirt, J. Mol Biol., 26, 365–369 (1967). Unreplicated plasmids are selectively destroyed by restriction with DpnI. Replicated plasmids are then recovered by transformation into competent bacteria.

Early passage NIH 3T3 mouse fibroblasts (ATCC# CRL 1658) and Rat 2 fibroblasts (ATCC# CRL 1764) were grown in DMEM supplemented with 10% bovine calf serum and 50 µg/ml gentamycin sulfate.

The DH10B E. coli used in the present invention are commercially available from GIBCO.

Construction of Plasmids:

Two basic plasmids were constructed for use in the present invention. The first (denoted $P_fLAG$) comprised a human promoter-regulated polyomavirus large T antigen gene which served as a source of large T antigen upon activation of the promoter, and was based on the human c-fos promoter. The second plasmid (denoted Lα2) was a retroviral cDNA expression vector containing the polyomavirus origin of replication.

The retroviral cDNA vector Lα2 was prepared as follows. Polyomavirus DNA strain A2 was digested with BamHI/NarI and the resulting 750 bp fragment was ligated into the BamHI/NarI sites in pUC19 to give a plasmid denoted pOri. The retroviral vector pMV7 was digested with FspI/AflIII and the resulting 4 kb band containing the two Moloney murine sarcoma virus LTRs was ligated into the HincII/AflIII fragment of pOri, to give a plasmid denoted pMV7-2. A neomycin resistance gene present between the two Moloney murine sarcoma virus LTRs in pMV7-2 was removed by SauI/ClaI digestion and replaced by a synthetic polylinker (described above) to give the plasmid pMV7-3. To enable blue-white screening, the polylinker in pUC19 was replaced with a NcoI linker, then the 360 bp lac Z region was removed by AseI/NarI digestion, blunt ended with mung bean nuclease, and ligated into the pMV7-3 polylinker. The resultant plasmid, denoted Lα2, was 4.5 kb and contained unique SalI and NotI sites at the 5' and 3' ends, respectively, of the lac Z gene. A translational start codon, followed by a DNA sequence encoding a histidine hexamer, was inserted 5' to the cDNA insertion site to insure expression of cDNA-encoded protein from truncated cDNA inserts lacking start codons, and to aid in subsequent protein purification.

The $P_fLAG$ plasmid was prepared via the following procedure. The polyomavirus large T antigen under the control of the human c-fos promoter was introduced by digesting the 5.9 kb BamHI fragment of pcfos-1, disclosed by Curran, et al., Mol. Cell. Biol., 3, 914–921(1983), with NaeI to remove the entire coding region of the c-fos gene and inserting the 2.8 kb BstXI/HincII band from polyomavirus, encoding the polyoma T antigen. Middle and small T expression was eliminated by inserting a stop codon in the ScaI site located at position 605 of the polyomavirus DNA sequence reported in Tooze, supra. The resulting construct was denoted $P_fLAG$-1 (for promoter$_{fos}$/large T antigen).

A third vector, denoted HEL, was prepared for use in identifying the intracellular locations of CROC-1. The histidine hexamer coding sequences of Lα2 were removed by BglII/SalI digestion and replaced with coding sequences for the nine amino acid influenza virus HA1 epitope described in Field, et al., Mol. Cell. Biol., 8, 2159–2165 (1988). The SV40 origin of replication was then inserted at the unique XbaI site between the polyoma origin of replication and the 5' LTR, to give HEL.

A fourth vector was prepared for use in confirming the ability of suspected human c-fos promoter activating proteins to stimulate the c-fos promoter. The fos-CAT reporter gene described by Deschamps, et al., in Science, 233, 1174–1177 (1985), was prepared by inserting the human c-fos promoter from the −735 (BamHI site) to +42 (NaeI site) in from of the bacterial CAT gene in the pCAT basic vector (Promega).

Determining Enhancer Requirements for $P_fLAG$-dependent Contingent Replication:

For purposes of the present invention, the human c-fos promoter in $P_fLAG$ must remain transcriptionally silent in quiescent cells, but be sensitive enough to respond to the low level expression of active, cDNA-encoded signalling molecules by producing sufficient T antigen to cause plasmid replication. The sensitivity and level of gene induction from the promoter can be increased by the incorporation of additional enhancer elements into the promoter. Multiple enhancer elements were incorporated into P₁LAG-1 by isolating an approximately 500 bp or more XhoI/BssHII(blunt-ended) fragment containing the c-fos enhancer elements, and ligating the enhancer region into the XhoI/SacII (blunt-ended) site of the previous P₁LAG.

To determine the number of enhancers required to display contingent replication, a series of P₁LAGs, containing 1, 2, 4 and 8 enhancer regions, were constructed. The following experiments were then conducted to define the enhancer requirements for P₁LAG-dependent contingent replication.

Muramatsu, et al., Mol. Cell. Biol., 9, 831–836 (1989) have shown that expression of the catalytic domain of protein kinase C induces the c-fos promoter. The nucleotide and deduced amino acid sequence of rat protein kinase C-β₁ are described in Housey, et al., Cell, 52, 343–354 (1988). The catalytic domain of rat protein kinase C-β₁ was incorporated into Lα2 to make a construct, denoted pMVPkCΔβ₁. Co-transfection of a pMVPkCΔβ₁/Lα2 mixture with a P₁LAG containing 1, 2, 4 or 8 enhancer regions would therefore provide a means of testing the sensitivity of each P₁LAG.

A threshold sensitivity of detecting about one plasmid out of forty for cDNA screening was used. Therefore a 1:40 (wt/wt) ratio of pMVPkCΔβ₁/Lα2 for co-transfection with each of the P₁LAGs into NIH 3T3 cells was utilized in the procedure described below. Cells were incubated for forty-eight (48) hours following transfection. The plasmids were extracted and examined, following DpnI digestion, for elevated plasmid recovery indicative of contingent replication. The results obtained under these conditions are presented in Table 1. These data show that eight enhancer regions (P₁LAG-8) were required for significant activation of plasmid replication, permitting an eight-fold increase in plasmid recovery over background resulting from co-transfection of P₁LAG-8 with vector alone. Induction with P₁LAG-8 ranged from 6-fold to greater than 20-fold increases in plasmid recovery, depending primarily on the level of background.

TABLE 1

Human c-fos enhancer requirement to activate polyomavirus large T antigen-activated contingent replication.*

| Plasmid Construct | No. of Enhancer Regions | Co-transfected Plasmid | Total Number of Colonies |
|---|---|---|---|
| P₁LAG-1 | 1 | pMV7-Z | 8 |
| P₁LAG-1 | 1 | pMV7PkCΔβ₁ Lα2 | 5 |
| P₁LAG-2 | 2 | pMV7-Z | 33 |
| P₁LAG-2 | 2 | pMV7PkCΔβ₁ Lα2 | 22 |
| P₁LAG-4 | 4 | pMV7-Z | 109 |
| P₁LAG-4 | 4 | pMV7PkCΔβ₁ Lα2 | 101 |
| P₁LAG-8 | 8 | pMV7-Z | 363 |
| P₁LAG-8 | 8 | pMV7PkCΔβ₁ Lα2 | 1915 |
| — | — | pMV7PkCΔβ₁ Lα2 | 7 |

*2 μg P₁LAG is co-transfected with 18 μg of either pMV7-Z or a 1:40 (wt/wt) ratio of pMV7PkCΔβ₁/Lα2. The results presented are the average of two experiments.

The effect of the concentration of plasmids encoding a promoter activating protein on the recovery of pMVPkCΔβ₁ within a total population of plasmids is determined by varying the concentration of pMVPkCΔβ₁ in a pMVPkCΔβ₁/Lα2 mixture prior to co-transfection with P₁LAG-8. Because Lα2 has a modified lac Z gene derived from pUC19, bacteria transformed with Lα2 will turn blue, whereas bacteria transformed with pMVPkCΔβ₁ will remain white, when plated on agar plates containing ampicillin, X-gal, and IPTG. The percentage of pMVPkCΔβ₁ is determined by expressing the number of white colonies as a percentage of total colonies formed after bacterial transformation of DpnI-digested Hirt extracts.

Experiments were conducted by co-transfecting P₁LAG-8 with the pMV7PkCΔβ₁/Lα2 mixtures beginning at a 1:80 ratio (wt/wt), then diluting down to a 1:400 ratio, using the methods described below. Competent DH10B E. coli were transformed with DpnI-digested Hirt extracts and plated on agar containing ampicillin, X-gal, and IPTG. The percent of pMV7PkCΔβ₁ in the recovered colonies was determined by the number of white colonies over the total colonies.

To insure that the white colonies resulted from transformation of pMVPkCΔβ₁, plasmids were recovered and restriction mapped. All white colonies showed the correct pMVPkCΔβ₁ restriction pattern. The results presented in Table 2 show that although the number of recovered colonies is reduced to background levels at high pMV7PkΔβ₁ dilution, the actual percentage of pMV7PkΔβ₁ colonies increases; indicating that a minimum of 400 library colonies can be transfected with P₁LAG-8 to enrich a cDNA library population for cDNA encoding signal transducing molecules. Initial cDNA library screening was therefore performed with plasmid pools comprised of four hundred or more plasmids in order to acquire a library population enriched in cDNAs encoding activators of the c-fos promoter.

TABLE 2

Concentration dependence of pMV7PkCΔβ₁ on plasmid recovery.*

| Ratio of co-transfected pMV7PkCΔβ₁/Lα2 | Number of Colonies | | Percent pMV7PkCΔβ₁ | Colonies per Dish |
|---|---|---|---|---|
| | Blue | White | | |
| 1:80 | 206 | 4 | 1.9 | 210 |
| 1:160 | 146 | 7 | 4.6 | 153 |
| 1:240 | 134 | 6 | 4.3 | 150 |
| 1:320 | 97 | 24 | 19.8 | 121 |
| 1:400 | 90 | 24 | 21.1 | 114 |

*Co-transfection with P₁LAG-8 and Lα2 alone gave a background of 102 colonies/dish in this experiment.

Cell Culture and Transfection:

For transfections, 8×10⁵ 3T3 cells were planted in growth medium in 100 mm dishes and allowed to attach overnight. The following day, transfections were performed by the method of Wigler, et al., Cell. 11, 223–232 (1977), using calcium phosphate. After a 4-hour exposure to the calcium phosphate precipitate, cells were washed twice with phosphate buffered saline, re-fed with DMEM supplemented with 0.5% bovine calf serum, and incubated at 37° C. for 40–48 hours. Cells were harvested and the plasmids were extracted by the procedure of Hirt, supra. The extracted plasmids were digested with DpnI for a minimum of 24 hours. DpnI digests were phenol extracted and ethanol precipitated. DNA was resuspended in 20 μL TE (1 mM EDTA+10 mM Tris, pH8.0), and transformed into competent DH10B bacteria (GIBCO).

Co-transfections were performed via the above procedure at a cDNA/P₁LAG ratio of 9:1 (wt/wt), using 20 μg DNA per dish.

cDNA Library Screening using Contingent Replication:

A human brain cDNA library was co-transefected with P̱LAG-8 into NIH 3T3 cells via the methods described above. Plasmid pools, comprised of approximately 30–40 plasmids, were co-transfected with P̱LAG-8 and examined for a minimum 5-fold increase in plasmid recovery. Plasmids from active pools were recovered and subdivided into secondary pools of four plasmids each, and similarly examined for activation of contingent replication. Plasmids from each active secondary pool were then examined individually for contingent replication. From approximately 1400 plasmids screened initially, two plasmids, denoted CROC-1 and CROC-2 (for contingent replication of cDNA), consistently gave elevated plasmid recovery when co-transfected with P̱LAG-8. The nucleotide sequence for CROC-1 is shown in SEQ ID NO:1.

A third plasmid, denoted CROC-4, was identified by further plasmid screening. Plasmid CROC-4 also consistently gave elevated plasmid recovery when co-transfected with P̱LAG-8. The nucelotide sequence for CROC-4 is shown in SEQ ID NO:3.

Confirmation of c-fos Promoter Activation using a fos-CAT Reporter Gene:

Certain extraneous factors could also cause the elevated plasmid recovery observed in the contingent replication assay. For example, incomplete bacterial methylation of the DpnI sites, which will confer DpnI resistance, or differences in transfection or transformation efficiency. To eliminate these possibilities, each of CROC-1, CROC-2 and CROC-4 was co-transfected with a fos-CAT reporter gene and tested for elevation of CAT activity as follows. Rat 2 cells were co-transfected with 18 μg Lα2-expressed cDNA (i.e., CROC-1, CROC-2 or CROC-4)+2 μg fos-CAT for 4 h, then refed with DMEM+0.5% calf serum. Cells were harvested 72 hours after transfection and CAT assays performed via the procedure of Gorman, et al., *Mol. Cell. Biol.*, 2, 1044–1051 (1982).

CAT activity was significantly induced by CROC-1, CROC-2 and CROC-4, indicative of c-fos promoter activation. The extent of activation was approximately 50% of the activation caused by co-transfection with pMVPkCAβ$_1$. In contrast, vector alone did not induce substantial CAT activity, nor did randomly chosen cDNA library plasmids isolated from the same plasmid pools as CROCs 1, 2 and 4, but which did not activate contingent replication. These results confirm that the elevated plasmid recovery observed upon co-transfection of CROCs 1, 2 or 4 with P̱LAG-8 was due to activation of the c-fos promoter in P̱LAG-mediated contingent replication.

Analysis of c-fos Activating Proteins:

Sequencing revealed that CROC-2 encodes the recently identified α$_2$-macroglobulin receptor-associated protein (AMRAP) disclosed in Strickland, et al., *J. Biol. Chem.*, 266, 13364–13369 (1991). The insert is nearly full length and extends from the start codon, which is in frame with the internal vector start codon, to the poly A tail.

A 347 base pair sequence corresponding to nucleotides 555–897 of CROC-4 has been submitted to GenBank (Accession #Z40809) as an expression sequence tag.

CROC-1 cDNA encodes a 19 kd protein with an acidic amino terminal half and a basic carboxy terminus, as shown in SEQ ID NO:1. The protein includes a kinase target domain which contains phosphorylation sites for a variety of kinases involved in signal transduction. Specifically, the kinase target region is comprised of adjacent proximal potential phosphorylation sites for: (a) tyrosine kinases (RXXXEXXXY motif, amino acids 81–89), Cooper, et al., *J. Biol. Chem.*, 259, 7835–7841 (1984); casein kinase 2 (TIYE motif, amino acids 82–85), Kuenzel, et al., *J. Biol. Chem.*, 262, 9136–9140 (1987); cAMP-dependent protein kinases (RIYS motif, amino acids 87–90) Glass, et al., *J. Biol. Chem.*, 261, 2987–2993 (1986) and Kishimoto, et al., *J. Biol. Chem.*, 260, 12492–12499 (1985); and protein kinase C (SLK motif, amino acids 90–92), Kishimoto, et al., supra.

The kinase target domain of the CROC-1 protein is a twelve amino acid stretch located at the start of the basic domain. The known transactivating ability of acidic domains in general, combined with the potential of basic domains to bind DNA, suggests that CROC-1 could function as a transcriptional activator whose activity is regulated by phosphorylation of the kinase target domain. Phosphorylation would cause a further increase in the acidity of the region, thereby enhancing its potential for transcriptional activation, as well as cause a change in the structural conformation of the protein.

The length and tissue distribution of CROC-1 mRNA was determined by Northern analysis of poly A-containing RNA, isolated from various human tissues, using the 1.8 kb SalI/NotI insert of CROC-1 as a probe. CROC-1 mRNA was approximately 2.3 kb in length, about 0.5 kb longer than our cDNA insert, and present in all tissues examined, with the highest levels being expressed in brain, skeletal muscle, and kidney. In comparison, the 1.5 kb CROC-2 mRNA was present in all tissues examined, but with the highest levels being expressed in heart, placenta, and kidney. No evidence was found for additional transcripts, as a result of alternative splicing or multiple sets of transcription-termination-polyadenylation signals, as reported for CROC-2 by Strickland, et al., supra.

Intracellular localization of the CROC-1 protein was determined by cloning CROC-1 in HEL and electroporating the resultant plasmid into COS-7 cells (ATCC# CRL 1651). Incorporation of CROC-1 nucleic acid into the HEL vector enables the in frame fusion of the hemagglutinin epitope to the CROC-1 protein. The intracellular location of CROC-1 protein was then determined by immunofluorescence microscopy using mouse monoclonal antibody directed against the hemagglutinin epitope. Electroporation of CROC-1 in HEL resulted in intense nuclear fluorescence. In contrast, electroporation of HEL alone resulted in general cytoplasmic fluorescence, indicating that nuclear localization is an inherent property of the CROC-1 protein.

The present invention encompasses modifications and variations which will be evident to those skilled in the art. The specific embodiments described herein are representative examples only, the scope of the present invention being defined by the claims.

We claim:

1. A mammalian cell line, the cells of which comprise:
    (a) a recombinant vector comprising an inducible or tissue specific promoter operatively linked to a nucleic acid encoding polyomavirus large T antigen, which nucleic acid has been modified to eliminate the expression of middle T antigen; and
    (b) a recombinant expression vector comprising a polyomavirus origin of replication and a nucleic acid to be assayed for encoding an activating protein of said promoter.

2. A mammalian cell line of claim 1 wherein the promoter is the human c-fos promoter.

3. A mammalian cell line of claim 2 wherein the recombinant vector is the plasmid PLAG-8.

4. A mammalian cell line of claim 1 wherein the expression vector is plasmid Lα2.

5. A method for identifying a nucleic acid encoding a promoter activating protein, comprising:
    (a) culturing a mammalian cell line of claim 1 under conditions in which such nucleic acids are expressed; and
    (b) measuring the levels of replicated vectors in the cells after a period of incubation sufficient to permit vector replication;
    whereby a nucleic acid encoding a promoter activating protein is identified by measurement of increased levels of vectors in the cells.

6. A method of claim 5 wherein the promoter is the human c-fos promoter.

7. A mammalian cell line, the cells of which comprise
    (a) a first recombinant expression vector comprising a reporter gene operatively linked to a human c-fos promoter; and
    (b) a second recombinant expression vector comprising a nucleic acid encoding a human c-fos promoter activating protein;
    wherein the second recombinant expression vector encodes the CROC-1 protein, the CROC-4 protein, or α2-macroglobulin receptor-associated protein.

8. A mammalian cell line of claim 7 comprising NIH 3T3 mouse cells.

9. A vector comprising a human c-fos promoter operatively liked to a nucleic acid encoding polyomavirus large T antigen, which nucleic acid has been modified to eliminate the expression of middle T antigen.

10. A vector of claim 9 which is the plasmid PLAG-8.

11. A recombinant expression vector comprising a reporter gene operatively linked to a human c-fos promoter.

12. A method for identifying an antagonist of a human c-fos promoter activating protein, comprising:
  (a) providing a mammalian cell line, the cells of which comprise
    (i) a first recombinant expression vector comprising a reporter gene operatively linked to a human c-fos promoter; and
    (ii) a second recombinant expression vector comprising a nucleic acid encoding a human c-fos promoter activating protein;
  (b) contacting the cell line of step (a) with a sample to be assayed for an antagonist of the human c-fos promoter activating protein; and
  (c) measuring the level of expression of the reporter gene; whereby an antagonist of the human c-fos promoter activating protein is identified by measurement of a reduced level of expression of the reporter gene.

13. The method of claim 12, wherein said human c-fos promoter activating protein is CROC-1, CROC-3 or α2-macroglobulin protein.

14. A human c-fos promoter activating protein having an amino acid sequence as defined by SEQ ID NO:1 or SEQ ID NO:3, or an antigenic fragment thereof.

15. An isolated nucleic acid encoding a protein of claim 11.

16. The nucleic acid of claim 15 having the nucleotide sequence as shown in SEQ ID NO:1 or SEQ ID NO:3.

17. The nucleic acid of claim 15 encoding a protein having an amino acid sequence defined by SEQ ID NO:1 or SEQ ID NO:3, or a conservatively modified variant thereof.

18. The protein of claim 14 having an amino acid sequence defined by SEQ ID NO:1.

19. The protein of claim 14 having an amino acid sequence defined by SEQ ID NO:3.

* * * * *

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
        ( A ) LENGTH: 1930 base pairs
        ( B ) TYPE: nucleic acid
        ( C ) STRANDEDNESS: double
        ( D ) TOPOLOGY: linear ( i i ) MOLECULE TYPE: cDNA ( i i i ) SEQUENCE DESCRIPTION: SEQ ID NO:1:

```
ATG GAT CTC AGG CCT AGA TCT CAT CAC CAT CAC CAT CAT TGG TGC CAG     48
Met Asp Leu Arg Pro Arg Ser His His His His His His Trp Cys Gln
            5                   10                  15

TGT GCT GGT CGA CCC ACG CGT CCG GAT GGC AGC CAC CAC GGG CTC GGG     96
Cys Ala Gly Arg Pro Thr Arg Pro Asp Gly Ser His His Gly Leu Gly
                20                  25                  30

AGT AAA AGT CCC TCG CAA TTT CGA CTG TTG GAA GAA CTC GAA GAA GGC    144
Ser Lys Ser Pro Ser Gln Phe Arg Leu Leu Glu Glu Leu Glu Glu Gly
            35                  40                  45

CAG AAA GGA GTA GGA GAT GGC ACA GTT AGC TGG GGT CTA GAA GAT GAC    192
Gln Lys Gly Val Gly Asp Gly Thr Val Ser Trp Gly Leu Glu Asp Asp
    50                  55                      60

GAA GAC ATG ACA CTT ACA AGA TGG ACA GGG ATG ATA ATT GGG CCT CCA    240
Glu Asp Met Thr Leu Thr Arg Trp Thr Gly Met Ile Ile Gly Pro Pro
65              70                  75                      80

AGA ACA ATT TAT GAA AAC CGA ATA TAC AGC CTT AAA ATA GAA TGT GGA    288
Arg Thr Ile Tyr Glu Asn Arg Ile Tyr Ser Leu Lys Ile Glu Cys Gly
                85                  90                  95

CCT AAA TAC CCA GAA GCA CCC CCT TTT GTA AGA TTT GTA ACA AAA ATT    336
Pro Lys Tyr Pro Glu Ala Pro Pro Phe Val Arg Phe Val Thr Lys Ile
            100                 105                 110

AAT ATG AAT GGA GTA AAT AGT TCT AAT GGA GTG GTG GAC CCA AGA GCC    384
Asn Met Asn Gly Val Asn Ser Ser Asn Gly Val Val Asp Pro Arg Ala
            115                 120                 125

ATA TCA GTG CTA GCA AAA TGG CAG AAT TCA TAT AGC ATC AAA GTT GTC    432
Ile Ser Val Leu Ala Lys Trp Gln Asn Ser Tyr Ser Ile Lys Val Val
    130                 135                 140

CTG CAA GAG CTT CGG CGC CTA ATG ATG TCT AAA GAA AAT ATG AAA CTC    480
Leu Gln Glu Leu Arg Arg Leu Met Met Ser Lys Glu Asn Met Lys Leu
145                 150                 155                 160

CCT CAG CCG CCC GAA GGA CAG TGT TAC AGC AAT TAA TCA AAA AGA AAA    528
Pro Gln Pro Pro Glu Gly Gln Cys Tyr Ser Asn ***
            165                 170

ACC ACA GGC CCT TCC CCT TCC CCC CAA TTC GAT TTA ATC AGT CTT CAT    576

TTT CCA CAG TAG TAA ATT TTC TAG ATA CGT CTT GTA GAC CTC AAA GTA    624

CCG GAA AGG AAG CTC CCA TTC AAA GGA AAT TTA TCT TAA GAT ACT GTA    672

AAT GAT ACT AAT TTT TTG TCC ATT TGA AAT ATA TAA GTT GTG CTA TAA    720

CAA ATC ATC CTG TCA AGT GTA ACC ACT GTC CAC GTA GTT GAA CTT CTG    768

GGA TCA AGA AAG TCT ATT TAA ATT GAT TCC CAT CAT AAC TGG TGG GGC    816

ACA TCT AAC TCA ACT GTG AAA AGA CAC ATC ACA CAA TCA CCT TGC TGC    864

TGA TTA CAC GGC CTG GGG TCT CTG CCT TCT CCC TTT ACC CTC CCG CCT    912
```

-continued

```
CCC ACC CTC CCT GCA ACA ACA GCC CTC TAG CCT GGG GGG CTT GTT AGA        960
GTA GAT GTG AAG GTT TCA GGT CGC AGC CTG TGG GAC TAC TGC TAG GTG       1008
TGT GGG GTG TTT CGC CTG CAC CCC TGG TTC CTT TAA GTC TTA AGT GAT       1056
GCC CCT TCC AAA CCA TCA TCC TGT CCC CAC GCT CCT CCA CTC CCG CCC       1104
TTG GCC GAA GCA TAG ATT GTA ACC CCT CCA CTC CCC TCT GAG ATT GGC       1152
TTC GGT GAG GAA TTC AGG GCT TTC CCC ATA TCT TCT CTC CCC CCA CCT       1200
TTA TCG AGG GGT GCT GCT TTT TCT CCC TCC TCC TCA AGT TCC TTT TTG       1248
CAC CGT CAC CAC CCA ACA CCT TCC ATG ACA CTT CCT TGC TTT GGC CAG       1296
AAG CCA TCA GGT AAG GTT GGA AAG AGC CTC TGA CCT CCC TTG TTT AGT       1344
TTT GGA ACC ATA CTC ACT CAC TCT CCA CCA GCC TGG GAA ATG AAT ATT       1392
GGG TCC TCA GCC CTG CCA CCC TCT GCT GTC ATC AGC TGA TGC ATT GTT       1440
TTT AGC TCA GGT TTT GAT AAG GTG AAA AGA ATA GTC ACC AGG GTT ACT       1488
CAG ACC TGC CAG CTC TCG GAG TCC TTG GTG GTT GAA CTT GGA GAA AGA       1536
CCG CAT GAA GAT ACT TGT AAG CAC ACA TGA TCC CTC TGA ATT GTT TTA       1584
CTT TCC TGT AAC TGC TTT TGC TTT TAA AAA TTG AAG AAG TTT TAA ACA       1632
GGG CTT TCA TTT GGT CAT CCT TGC AAT CCA TTG GGG TCT AGT TTG GAA       1680
TCT GAC AAC TGG AAC AAA AAG AAC CTT GAA TCC GGT GCA TGC CTT GGT       1728
TTT GGT GCT GCT GCT GCT TCC CAA GAT CCT CAG CAG GGA TTA AGA AGG       1776
AAC CCG GTG TGC ACA GCA GAT CCC CGA AAT TGG TGG GCT TGA CCT CCT       1824
GGC AAA TTG CTG CGT CTT TCC ACT TGC TGT TCA GGA CCA CTA AAT GCG       1872
AAA TGT GGA TGC ATA CCG AAA TAA AAG CAA TTC ATT GTG TAC TAA AAA       1920
AAA AAA AAA A                                                          1930
```

( 2 ) INFORMATION FOR SEQ ID NO: 2:

( i ) SEQUENCE CHARACTERISTICS:
        ( A ) LENGTH: 69 base pairs
        ( B ) TYPE: nucleic acid
        ( C ) STRANDEDNESS: double
        ( D ) TOPOLOGY: linear ( i i ) MOLECULE TYPE: DNA ( i i i ) SEQUENCE DESCRIPTION: SEQ ID NO:2:

```
CAC GTG AAT TCA AGA TCT CTG CAG AAG CTT TCC GGA CCG GGC CGC GTA        48
GCA CGC GTA ATA ATT ATC GAT                                            69
```

( 2 ) INFORMATION FOR SEQ ID NO: 3:

( i ) SEQUENCE CHARACTERISTICS:
        ( A ) LENGTH: 925 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:3:

```
GTCGACCCAC GCGTCCGCTC CTCACAGAAG CCTGGAGCTG GGCATCCAAG AAGAAGCAGC        60
CTCATTTGTT TTCTGGTGTC ATCGTAGGTG GCCACCTATG GCTTTTGGGA ATGTAAAAAG       120
GGCAGCTCTC TGGC ATG TTC CTG ACT GAG GAT CTC ATA ACA TTT AAC TTG        170
               Met Phe Leu Thr Glu Asp Leu Ile Thr Phe Asn Leu
                 5                          10
```

-continued

```
AGG AAC TTC CTC CTT TTC CAG CTT TGG GAG TCA AGC TTC TCA CCT GGG       218
Arg Asn Phe Leu Leu Phe Gln Leu Trp Glu Ser Ser Phe Ser Pro Gly
     15              20              25

GCG GGT GGG TTC TGC ACC ACC CTC CCA CCC TCC TTC CTC CGT GTG GAC       266
Ala Gly Gly Phe Cys Thr Thr Leu Pro Pro Ser Phe Leu Arg Val Asp
 30              35              40

GAT AGA GCC ACA TCC AGC ACC ACG GAC AGC TCC CGG GCG CCT TCA TCT       314
Asp Arg Ala Thr Ser Ser Thr Thr Asp Ser Ser Arg Ala Pro Ser Ser
 45              50              55              60

CCT CGT CCT CCA GGC AGC ACA AGC CAT TGT GGA ATC TCC ACC AGG TGT       362
Pro Arg Pro Pro Gly Ser Thr Ser His Cys Gly Ile Ser Thr Arg Cys
                 65              70              75

ACA GAA CGG TGC CTC TGC GTC CTG CCA CTC AGG ACC TCT CAA GTC CCC       410
Thr Glu Arg Cys Leu Cys Val Leu Pro Leu Arg Thr Ser Gln Val Pro
             80              85              90

GAT GTG ATG GCT CCT CAG CAT GAT CAG GAG AAA TTC CAT GAT CTT GCT       458
Asp Val Met Ala Pro Gln His Asp Gln Glu Lys Phe His Asp Leu Ala
         95             100             105

TAT TCC TGT CTT GGG AAG TCC TTC TCC ATG TCT AAC CAA GAT CTA TAT       506
Tyr Ser Cys Leu Gly Lys Ser Phe Ser Met Ser Asn Gln Asp Leu Tyr
    110             115             120

GGC TAT AGC ACC AGC TCT TTG GCT CTT GGC TTG GCA TGG CTA AGT TGG       554
Gly Tyr Ser Thr Ser Ser Leu Ala Leu Gly Leu Ala Trp Leu Ser Trp
125             130             135             140

GAG ACC AAA AAG AAG AAT GTA CTT CAT CTG GTT GGG CTG GAT TCC CTC       602
Glu Thr Lys Lys Lys Asn Val Leu His Leu Val Gly Leu Asp Ser Leu
                145             150             155

TGATAAGCCT TCCCAGTTGA CTGAAAGATG AGGCTAGGCT CTAGCAAGTT GAAGTCAAAC     662
***

CAGCTCCTTC AAGAAGCTTT GAGCAGAATG AAGTGGGGAG GACCCAGCTT CCAGCCCAGG     722

AAGCCCACTG TACCTGGAGC CATCTGGGAT AAGACTTTGA CCCATGACTC CCATATCCAC     782

AGCCTGTCCA TCCTAGCCCA TCCCAGTTTA TCCTGTATCA TTTGAGCTGG GATTCCCACA     842

TCCTCTGAGT TGGAAGTCCC ATCTCAAGTC TTCAATAAAG ACTCTTGAAT ATTGAAAAAA     902

AAAAAAAAAA AAAGGGCGGC CGC                                             925
```